(12) United States Patent
Sugizaki

(10) Patent No.: US 7,952,082 B2
(45) Date of Patent: May 31, 2011

(54) SAMPLE PREPARATION SYSTEM

(75) Inventor: Hideo Sugizaki, Tokyo (JP)

(73) Assignee: JEOL Ltd., Tokyo (JP)

( * ) Notice: Subject to any disclaimer, the term of this patent is extended or adjusted under 35 U.S.C. 154(b) by 649 days.

(21) Appl. No.: 11/876,033

(22) Filed: Oct. 22, 2007

(65) Prior Publication Data

US 2008/0099695 A1    May 1, 2008

(30) Foreign Application Priority Data

Oct. 26, 2006  (JP) ................................. 2006-291012

(51) Int. Cl.
*G21G 5/00* (2006.01)
(52) U.S. Cl. ......................... 250/492.1; 355/53; 318/640
(58) Field of Classification Search ................ 250/492.1
See application file for complete search history.

(56) References Cited

U.S. PATENT DOCUMENTS

| 4,191,916 | A | * | 3/1980 | Zasio et al. | 318/640 |
| 6,207,959 | B1 | * | 3/2001 | Satoh et al. | 250/442.11 |
| 6,900,444 | B2 | * | 5/2005 | Ferrara et al. | 250/491.1 |
| 7,015,483 | B2 | * | 3/2006 | Suzuki et al. | 250/311 |
| 7,217,934 | B2 | * | 5/2007 | Mori | 250/440.11 |
| 7,462,846 | B2 | * | 12/2008 | Park | 250/492.21 |
| 2005/0118065 | A1 | | 6/2005 | Hasegawa et al. | |

FOREIGN PATENT DOCUMENTS

JP   2005-037164   2/2005

* cited by examiner

*Primary Examiner* — Phillip A Johnston
(74) *Attorney, Agent, or Firm* — The Webb Law Firm

(57) ABSTRACT

A sample preparation system in which an ion beam is made to hit the surface of a sample while rotating the sample about an axis perpendicular to the processed surface of the sample under the condition where the processed surface of the sample is not perpendicular to the beam. The preparation system has a rotating mechanism and a tilting mechanism both of which are mounted in an enclosure mounted to the vacuum chamber. The rotating mechanism rotates the holder about the X-axis perpendicular to the surface of the holder on which the sample is placed. The tilting mechanism tilts the holder about the Y-axis perpendicular to the X-axis.

6 Claims, 4 Drawing Sheets

SAMPLE PREPARATION SYSTEM

BACKGROUND OF THE INVENTION

1. Field of the Invention

The present invention relates to a sample preparation system for processing a sample placed in position in a sample holder within a vacuum chamber by irradiating the sample with an ion beam.

2. Description of Related Art

A sample preparation system is described in Japanese Patent Laid-Open No. 2005-037164 for preparing a sample to be observed on a scanning electron microscope (SEM) or transmission electron microscope (TEM) comprising etching a sample by irradiating it with an ion beam. The sample is processed into a shape adapted for SEM imaging or TEM imaging.

With the aforementioned sample preparation system, when the sample is exchanged within atmosphere, the tilt angle of the surface of the sample to be processed with respect to the ion beam is adjusted. Then, the sample is set within a vacuum chamber. The chamber is evacuated. Subsequently, the sample is prepared. Therefore, there is the problem that the tilt angle cannot be reset with simple manipulations.

SUMMARY OF THE INVENTION

It is an object of the present invention to provide a sample preparation system that can be easily manipulated.

One embodiment of the present invention which achieves the above object provides a sample preparation system in which a processed surface of a sample is irradiated with an ion beam within a vacuum chamber such that the surface of the sample is not perpendicular to the ion beam and that the beam is made to hit the processed surface of the sample while rotating the sample about an axis perpendicular to the processed surface of the sample. The sample preparation system has a rotating mechanism for rotating the sample holder about a first axis perpendicular to the surface of the sample holder carrying the sample thereon and a tilting mechanism for tilting the sample holder about a second axis perpendicular to the first axis. The rotating mechanism and the tilting mechanism are mounted in an enclosure in which the sample holder is mounted. The enclosure is mounted in the vacuum chamber.

With this sample preparation system according to one embodiment of the present invention, the tilt angle of the sample surface can be reset with simple manipulations.

Other objects and features of the invention will appear in the course of the description thereof, which follows.

DESCRIPTION OF THE PREFERRED EMBODIMENTS

Figure 1:
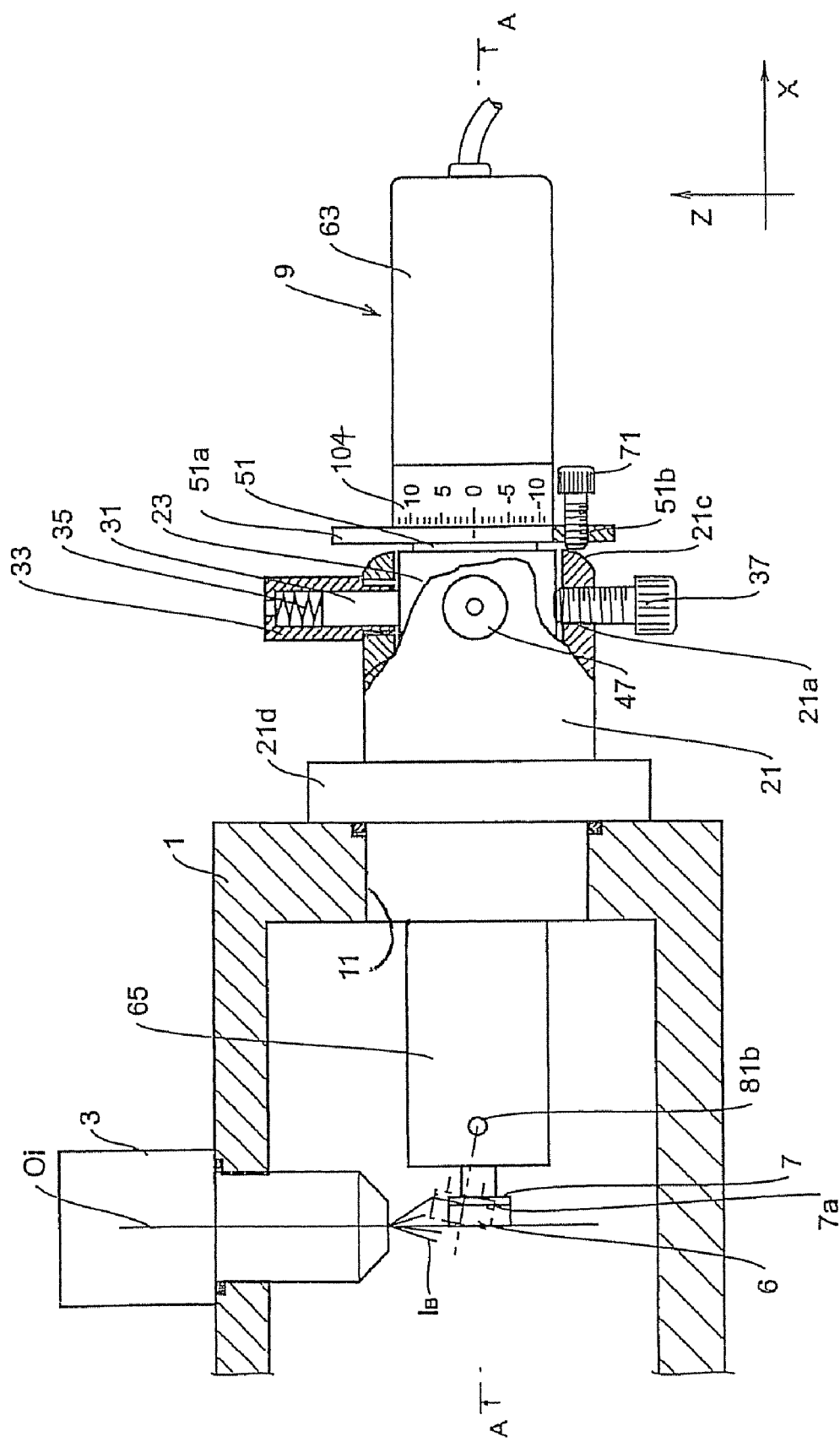
FIG. 1 is a side elevation partially in cross section of a sample preparation system according to one embodiment of the present invention, showing the whole structure of the system.
Figure 2:
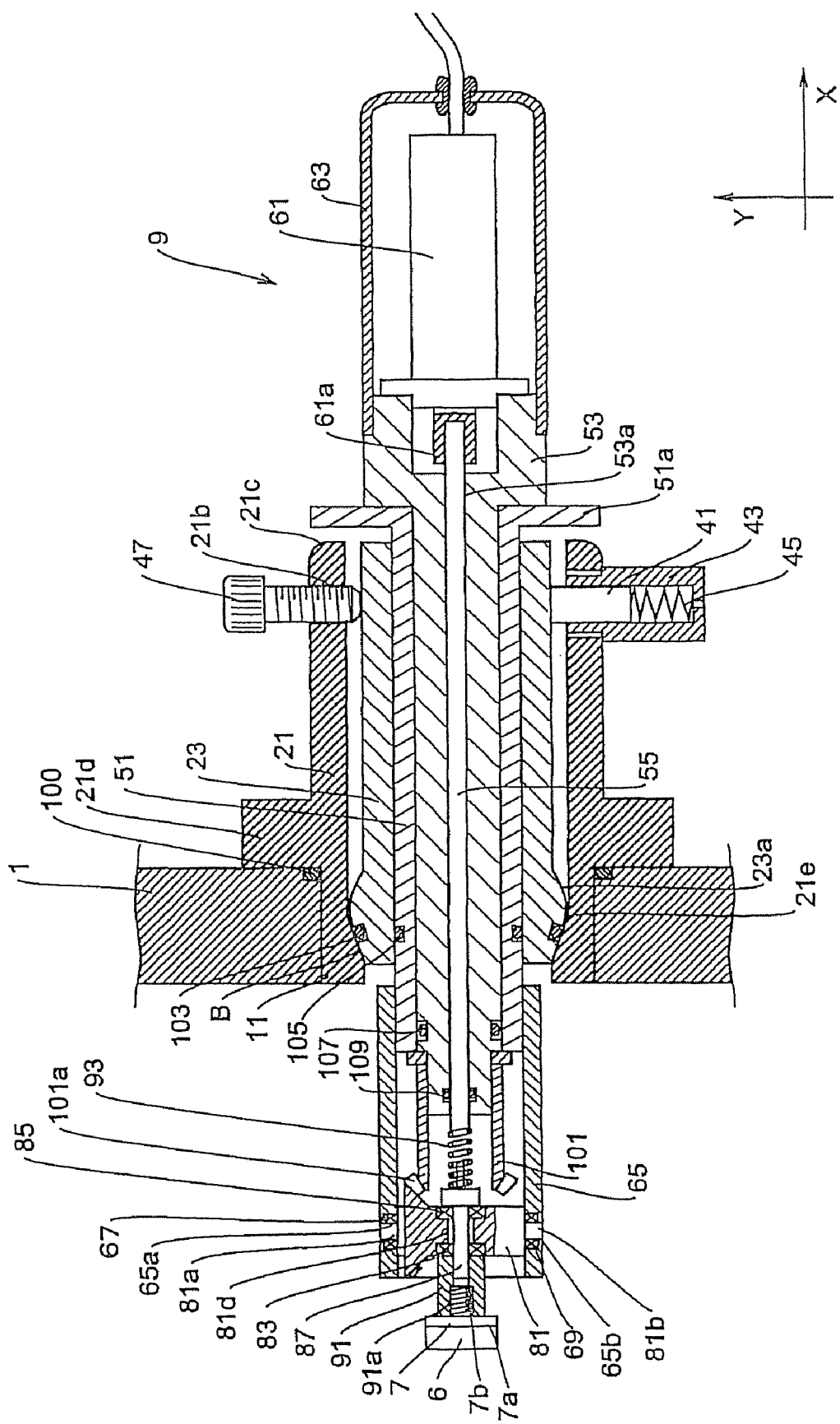
FIG. 2 is a cross-sectional view taken on line A-A of FIG. 1.
Figure 3:
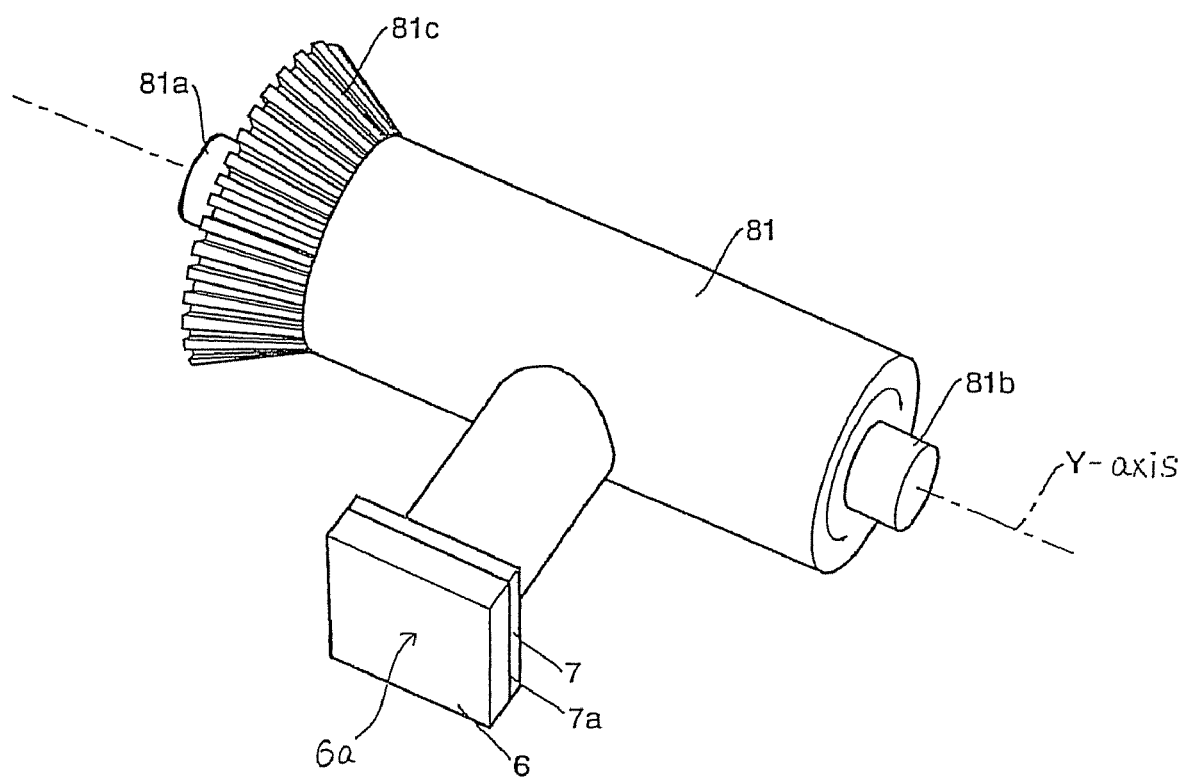
FIG. 3 is a perspective view of a tiltable block shown in FIG. 2.

A sample preparation system according to one embodiment of the present invention is first described by referring to FIGS. 1-3. FIG. 1 is a side elevation partially in cross section of the sample preparation system, showing the whole structure of the system.

FIG. 2 is a cross-sectional view taken on line A-A of FIG. 1. FIG. 3 is a perspective view of a tiltable block shown in FIG. 2. In FIG. 1, the up-and-down direction in the figure is the Z-axis direction. The right-and-left direction is the X-axis direction. In FIG. 2, the up-and-down direction is the Y-axis direction. The right-and-left direction is the X-axis direction.

The whole structure is first described by referring to FIG. 1. An ion source 3 forming an ion beam irradiation means is mounted to the top surface of a vacuum chamber 1. A gas ion source is used as the ion source 3. For example, a gas ion gun for ionizing Ar gas by electric discharge to release Ar ions is used. The center axis Oi of an ion beam $I_B$ released from the ion source 3 is substantially parallel to the Z-axis.

A cylindrical enclosure 9 is mounted to a side of the vacuum chamber 1. A sample holder 7 in which a sample 6 is set is mounted to the enclosure 9. The holder 7 has a surface 7a on which the sample 6 is placed. In the present embodiment, a first axis perpendicular to the surface 7a of the holder 7 is the X-axis. A second axis perpendicular to the first axis is the Y-axis.

The mechanism within the enclosure 9 is now described by referring to FIGS. 1 and 2. A hole 11 is formed in a side surface of the vacuum chamber 1. A cylindrical base 21 having a flanged portion 21d is mounted from outside the vacuum chamber 1.

A cylindrical sub-base 23 (see FIG. 2) is disposed in the inner cylindrical portion of the base 21. A receiver portion 21e in the form of a spherical surface is formed in the inner surface of the base 21. A pushing portion 23a in the form of a spherical surface is formed at one end of the sub-base 23, the pushing portion 23a being capable of coming into abutment with the receiver portion 21e of the base 21. Therefore, the sub-base 23 can process about its portion B in abutment with the base 21.

As shown in FIG. 1, a cylindrical plunger 31 extending along the Z-axis is mounted to the sub-base 23 that is outside the vacuum chamber 1. Meanwhile, a cylindrical guide 33 having a bottom is mounted to the base 21. The plunger 31 movably engages the guide 33. A spring 35 abutting against the front end of the plunger 31 is disposed at the bottom of the guide 33.

An internally threaded hole 21a extending along the Z-axis is formed circumferentially of the base 21 in the portion of the base 21 that is opposite to the portion to which the guide 33 is mounted. An adjusting screw 37 is screwed in the internally threaded hole 21a. The adjusting screw 37 pushes against the outer surface of the sub-base 23. Consequently, the sub-base 23 rotates in the Z-axis direction about its portion B in abutment with the base 21 in the Z-X plane.

Then, as shown in FIG. 2, a cylindrical plunger 41 extending along the Y-axis is mounted to the sub-base 23 that is located outside the vacuum chamber 1. Meanwhile, a cylindrical guide 43 having a bottom is mounted to the base 21. The plunger 41 movably engages the guide 43. A spring 45 abutting against the front end of the plunger 41 is disposed at the bottom of the guide 43.

An internally threaded hole 21b extending along the Y-axis is formed circumferentially of the base 21 in the portion of the base 21 opposite to the portion where the guide 43 is mounted. An adjusting screw 47 is screwed in the internally threaded hole 21b. The adjusting screw 47 pushes against the outer surface of the sub-base 23. Consequently, the sub-base 23 rotates in the Y-axis direction about the portion B in abutment with the base 21 within the X-Y plane.

As shown in FIG. 2, a cylindrical first pipe member 51 is axially (in the X-axis direction) movably mounted on the inner surface of the sub-base 23. One end of the first pipe member 51 is located inside the vacuum chamber 1. A cylindrical shaft-holding member 53 is mounted inside the first pipe member 51 so as to be rotatable relative to the first pipe member 51 about the X-axis. The shaft-holding member 53 is movable axially of the first pipe member 51 (i.e., in the X-axis direction). One end of the shaft-holding member 53 is also located within the vacuum chamber 1. A first shaft 55 is rotatably held in a hole 53a extending through the shaft-holding member 53 along its cylindrical axis.

A motor 61 is mounted to the end of the shaft-holding member 53 located outside the vacuum chamber 1. The output shaft 61a of the motor 61 is connected to the first shaft 55. Therefore, when the motor 61 is driven, the first shaft 55 is rotationally driven. A cover 63 covers the motor 61 and is mounted to the shaft-holding member 53. The cover 63 rotates together with the shaft-holding member 53.

As shown in FIG. 1, a flanged portion 51a opposite to an end of the base 21 is formed at the end of the first pipe member 51 that is closer to the motor 61. The end 21c of the base 21 to which the flanged portion 51a is opposite is shaped like a spherical surface.

An internally threaded hole 51b is formed in the flanged portion 51a of the first pipe member 51. An adjusting screw 71 is screwed in the internally threaded hole 51b. The adjusting screw 71 pushes against the end 21c of the base 21. Thus, the first pipe member 51 and the shaft-holding member 53 move in the X-axis direction within the X-Y plane.

A second pipe member 65 is mounted in the end of the first pipe member 51 that is located in the vacuum chamber 1. As shown in FIG. 2, holes 65a and 65b are formed in the wall of the second pipe member 65 of circular cross section and extend in the Y-axis direction. Bearings 67 and 69 are mounted in the holes 65a and 65b, respectively. A tiltable block 81 is disposed inside the second pipe member 65. Protrusive portions 81a and 81b are formed at the opposite ends of the tiltable block 81 and are rotatably engaged in the holes 65a and 65b in the second pipe member 65 via bearings 67 and 69 as shown in FIG. 3. The tiltable block 81 can tilt relative to the second pipe member 65 about the Y-axis.

A hole 81d extends through the tiltable block 81 in the X-axis direction. Bearings 83 and 85 are formed in the hole 81d. A second shaft 87 is rotatably held in the bearings 83 and 85.

A sleeve 91 is mounted to one end of the second shaft 87. The second shaft 87 and sleeve 91 rotate as a unit. An internally threaded hole 91a is formed in the sleeve 91. The sample holder 7 has an externally threaded portion 7b that is in threaded engagement in the internally threaded hole 91a. The second shaft 78, sleeve 91, and sample holder 7 rotate as a unit.

The first shaft 55 and second shaft 87 are connected via a universal coupling 93 that resembles a coil spring.

A cylindrical third pipe member 101 is mounted to the end of the shaft-holding member 53 that is on the side of the vacuum chamber 1. The third pipe member 101 rotates together with the shaft-holding member 53. A bevel gear portion 101a having a bevel gear about the axis (X-axis) of the third pipe member 101 is formed at the front end of the third pipe member 101.

As shown in FIG. 3, a bevel gear portion 81c coming into threaded engagement with the bevel gear portion 101a of the third pipe member 101 is formed on the tiltable block 81 about the Y-axis.

When the portion of the shaft-holding member 53 located outside the vacuum chamber 1 is rotated relative to the sub-base 23, the third pipe member 101 having the bevel gear portion 101a also rotates. Furthermore, the tiltable block 81 having the bevel gear portion 81c in threaded engagement with the bevel gear portion 101a is tilted about the Y-axis. In the present embodiment, a scale 104 is formed on the portion of the shaft-holding member 53 that is located outside the vacuum chamber 1 as shown in FIG. 1.

As shown in FIG. 2, airtightness between the vacuum chamber 1 and the base 21 is attained by an O-ring 100. Airtightness between the base 21 and the sub-base 23 is attained by an O-ring 103. Airtightness between the sub-base 23 and the first pipe member 51 is attained by an O-ring 105. Airtightness between the first pipe member 51 and the shaft-holding member 53 is attained by an O-ring 107. Airtightness between the shaft-holding member 53 and the first shaft 55 is attained by an O-ring 109.

The plunger 31, guide 33, spring 35, and adjusting screw 37 together form a Z-axis adjustment mechanism for moving the sub-base 23, i.e., the sample holder 7, relative to the base 21 in the Z-axis direction.

The plunger 41, guide 43, spring 45, and adjusting screw 47 together form a Y-axis adjustment mechanism for moving the sub-base 23, i.e., the sample holder 7, relative to the base 21 in the Y-axis direction.

The adjusting screw 71 forms an X-axis adjustment mechanism for moving the first pipe member 51 and the shaft-holding member 53, i.e., the sample holder 7, relative to the sub-base 23 in the X-axis direction.

The shaft-holding member 53, third pipe member 101, and tiltable block 81 together form a tilting mechanism for tilting the sample holder 7 about the Y-axis.

The operation of the structure constructed as described so far is described. When the enclosure 9 is set in the vacuum chamber 1 and the motor 61 is driven, rotation of the motor 61 is transmitted to the sample holder 7 via the output shaft 61a, first shaft 55, universal coupling 93, and second shaft 87. As a result, the sample 6 is rotated about the X-axis. That is, the rotating mechanism operates.

When the enclosure 9 is set in the vacuum chamber 1, if the adjusting screw 37 is rotated, the base 21, sub-base 23, first pipe member 51, and shaft-holding member 53 rotate in the Z-axis direction about a point B within the X-Z plane. The sample holder 7 is adjusted in the Z-axis direction. Thus, the Z-axis adjustment mechanism operates.

The base 21, sub-base 23, first pipe member 51, and shaft-holding member 53 are rotated about the point B in the Y-axis direction within the X-Y plane by rotating the adjusting screw 47. The sample holder 7 is adjusted in the Y-axis direction. That is, the Y-axis adjustment mechanism operates.

The sub-base 23, first pipe member 51, and shaft-holding member 53 are moved relative to the base 21 in the X-axis direction by rotating the adjusting screw 71. As a result, the sample holder 7 is adjusted in the X-axis direction. That is, the X-axis adjustment mechanism operates.

If the cover 63 located outside the vacuum chamber 1 is rotated relative to the sub-base 23, the sample holder 7 (i.e., the tiltable block 81) is tilted about the Y-axis by the tilting mechanism. As a result, the processed surface 6a (FIG. 3) of the sample is made non-parallel and non-perpendicular to the ion beam $I_B$ as indicated by the dotted line in FIG. 1. Under this condition, if the rotating mechanism is operated, the ion beam is made to hit the processed surface while rotating the sample about the axis perpendicular to the processed surface of the sample under the condition where the processed surface of the sample is non-perpendicular to the ion beam. As a result, the processed surface 6a of the sample is etched conically. The center of the processed surface 6a is etched most deeply. Alternatively, the ion beam may be made to hit the sample while rotating the sample without tilting the sample, i.e., under the condition where the processed surface 6a of the sample is kept parallel to the ion beam $I_B$. This beam irradiation is performed, for example, when the processed surface of the sample is cleaned.

In this structure, the adjusting screws 37, 47, 71 and cover 63 are mounted on the portions of the enclosure 9 which are outside the vacuum chamber 1. The screw 37 is the control portion of the Z-axis adjustment mechanism. The screw 47 is the control portion of the Y-axis adjustment mechanism. The screw 71 is the control portion of the X-axis adjustment mechanism. The cover 63 is the control portion of the tilting mechanism. Consequently, under the condition where the enclosure 9 is mounted to the vacuum chamber 1, the Z-axis adjustment mechanism, Y-axis adjustment mechanism, X-axis adjustment mechanism, and tilting mechanism can be manipulated easily.

Figure 4:
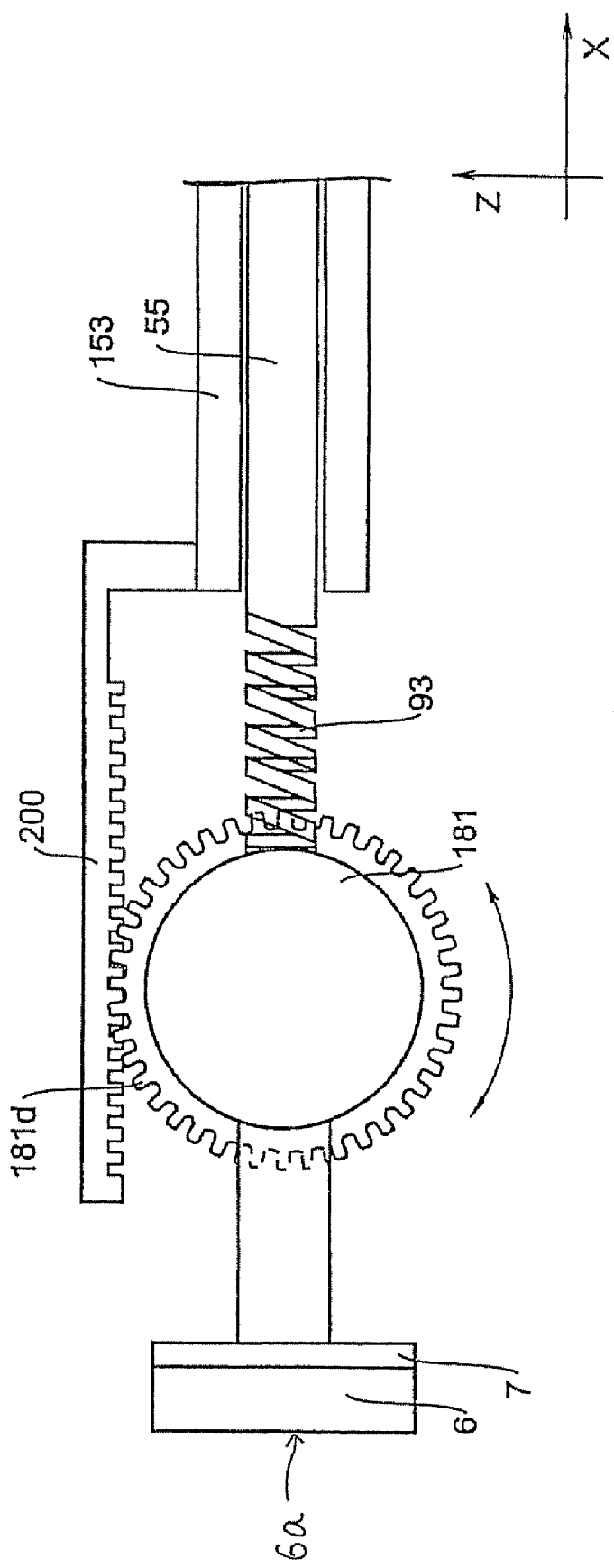
FIG. 4 is a side elevation of a sample preparation system according to another embodiment of the present invention.

It is to be understood that the present invention is not limited to the above embodiment. In the above embodiment, the tilting mechanism uses a bevel gear. This mechanism may be replaced by a structure shown in FIG. 4, where a tiltable block 181 has a pinion 181d about the axis of rotation (Y-axis) of the tiltable block 181. A rack 200 with which the pinion 181d is in threaded engagement is mounted to a holding member 153 that holds the first shaft 55. The holding member 153 can move along the first shaft 55, i.e., in the X-axis direction.

The rack 200 is moved in the X-axis direction by moving the holding member 153 in the X-direction. The tiltable block 181 having the pinion 181d in threaded engagement with the rack 200 rotates about the Y-axis to adjust the tilt of the sample 6.

Another tilting mechanism for tilting the sample holder may have a worm wheel on the side of the tiltable block. A worm in threaded engagement with the worm wheel is mounted along the first shaft. The worm may be rotated from outside the enclosure.

Having thus described my invention with the detail and particularity required by the Patent Laws, what is desired protected by Letters Patent is set forth in the following claims.

The invention claimed is:

1. A sample preparation system mounted on the wall of a vacuum chamber for irradiating a sample with an ion beam held within the vacuum chamber such that a surface of the sample to be processed may be adjustably positioned at an angle not perpendicular to the ion beam and that the beam is made to hit the processed sample while rotating the sample about an axis perpendicular to the processed surface of the sample, said sample preparation system comprising:
 a rotating mechanism for rotating the sample holder about a first axis perpendicular to a surface of the sample holder carrying the sample thereon; and
 a tilting mechanism for tilting the sample holder about a second axis perpendicular to the first axis,
 a cylindrical enclosure mounted in the wall of the vacuum chamber extending axially from both sides of the wall of the vacuum chamber wherein said rotating mechanism and said tilting mechanism are mounted in said cylindrical enclosure having the sample holder mounted therein at one end thereof, said sample holder extending out of the enclosure where it can be exposed to the ion beam, said cylindrical enclosure having an electric motor therein at the end opposite the sample holder, and a partially flexible drive shaft extending from the motor to the sample holder through the wall of the vacuum chamber.

2. A sample preparation system as set forth in claim 1, wherein said tilting mechanism has a control portion mounted on a portion of said cylindrical enclosure that is located outside said vacuum chamber being connected to the tilting mechanism by a hollow shaft extending to the tilting mechanism and enclosing the drive shaft.

3. A sample preparation system as set forth in claim 2, wherein a tiltable block is mounted in said enclosure to rotate about an axis perpendicular to the cylindrical axis of said cylindrical enclosure,
 wherein said sample holder is mounted to said tiltable block so as to be rotatable about said first axis, and
 wherein said tiltable block is rotationally driven by said hollow shaft and said tilting mechanism.

4. A sample preparation system as set forth in claim 3, wherein said tilting mechanism has a first gear mounted on an end of said hollow shaft and a second gear mounted on a side of said tiltable block, the second gear meshing with the first gear.

5. A sample preparation system as set forth in claim 4, wherein each of said first and second gears is a bevel gear.

6. A sample preparation system as set forth in claim 4, wherein said first gear is a rack, while said second gear is a pinion.

* * * * *